Figure 1:
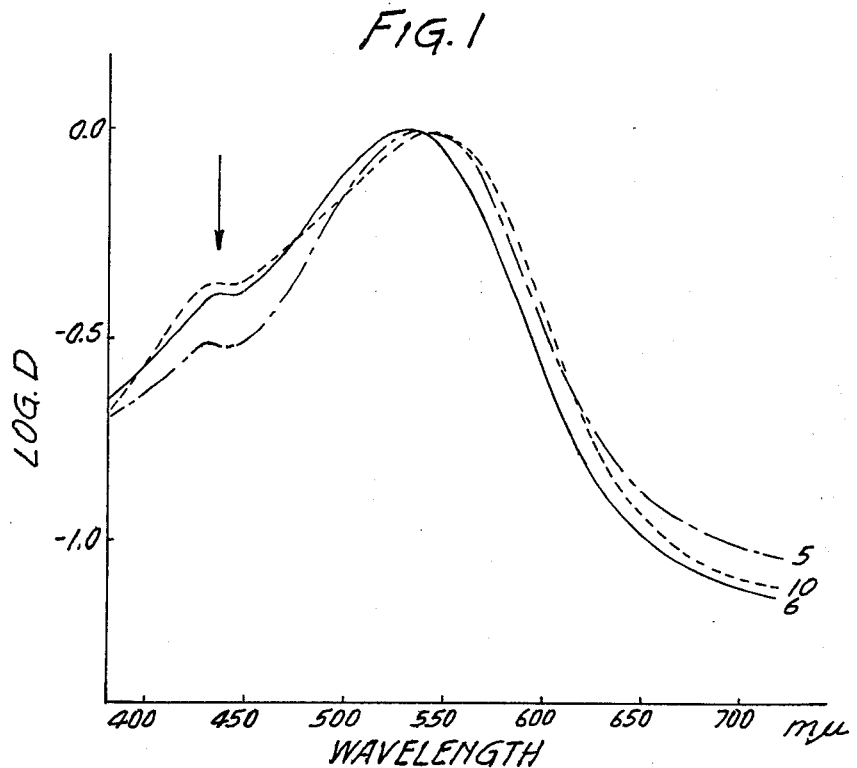

United States Patent [19]

Gandino et al.

[11] 3,939,176

[45] Feb. 17, 1976

[54] MAGENTA COUPLERS

[75] Inventors: Mario Gandino, Ferrania; Paolo Beretta, Liberta Ferrania, both of Italy

[73] Assignee: Minnesota Mining and Manufacturing Company, Saint Paul, Minn.

[22] Filed: July 22, 1974

[21] Appl. No.: 490,733

Related U.S. Application Data

[60] Division of Ser. No. 268,449, July 3, 1972, Pat. No. 3,844,794, which is a continuation of Ser. No. 43,031, June 3, 1970, abandoned.

[52] U.S. Cl. ............................................. 260/310 A
[51] Int. Cl.² ...................................... C07D 231/08
[58] Field of Search ............................... 260/310 A

[56] References Cited

UNITED STATES PATENTS

| | | | |
|---|---|---|---|
| 2,369,489 | 2/1945 | Porter et al. | 260/310 A |
| 3,062,653 | 11/1962 | Weissberger et al. | 260/310 A |
| 3,558,319 | 1/1971 | Hamaoka et al. | 260/310 A |
| 3,823,156 | 7/1974 | Oku et al. | 260/310 A |

*Primary Examiner*—Donald B. Moyer
*Attorney, Agent, or Firm*—Alexander, Sell, Steldt & Delahunt

[57] ABSTRACT

Magenta couplers of the 5-pyrazolone type which have a phenylcarbamylamino substituent in the 3-position of the pyrazolone nucleus and which have, as a substituent in the 1-position of the pyrazolone nucleus, a 2′, 4′-dihalo-6′-alkoxyphenyl group or a 2′, 6′-dihalo-4′-alkoxyphenyl group.

4 Claims, 4 Drawing Figures

MAGENTA COUPLERS

This is a division of application Ser. No. 268,449, filed July 3, 1972, now U.S. Pat. No. 3,844,794, which is a continuation of Ser. No. 43,031, filed June 3, 1970, now abandoned.

The present invention relates to photographic couplers and more specifically to couplers which react with an oxidation product of developers of the paraphenylene diamine type to provide magenta dyes.

The formation of colored photographic images by the reaction between photographic color couplers and oxidation products of developers of the paraphenylene diamine type, is well known in silver halide color photographic technology. In the subtractive color process, such images are colored, respectively, yellow, magenta and cyan, which colors are complementary of the three primary colors blue, green and red. Good color reproduction requires the three images to appear as a "balanced" whole. To achieve such a color "balance", couplers must often be employed which provide magenta dyes having absorption maxima which are shifted sometimes towards higher and sometimes towards lower wavelengths and which exhibit absorption curves which contain little if any undesired secondary absorption. Magenta dyes have been produced from couplers of the 1-phenyl-3-acylamino-5-pyrazolone type, as shown by U.S. Pat. Nos. 2,348,463; 2,369,489; 2,511,231; 2,600,788; 3,062,653; and British Pat. No. 904,852. Certain of these patents describe efforts to vary coupler properties by varying substituent groups of the couplers.

Good color reproduction also requires dyes which yield good image contrast and high image color density. In addition, it is essential from preservation of the colored images that the dyes which are derived from couplers have good stability characteristics. Briefly, the present invention provides a 5-pyrazolone coupler having a 5-pyrazolone nucleus which contains in the 3-position thereof a phenylcarbamylamino group and which contains in the 1-position thereof a 2',4'-dihalo-6'-alkoxyphenyl group or a 2',6'-dihalo-4'-alkoxyphenyl group.

The preferred couplers of the present invention may be represented by the general formula

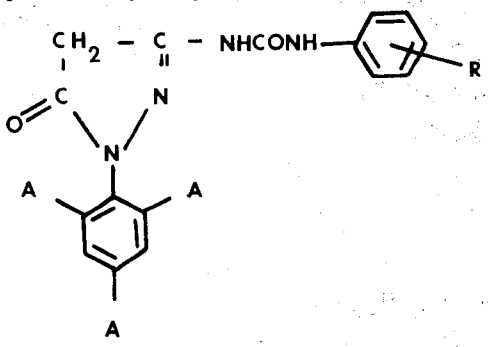

wherein two of the A groups are halogen, the remaining A group is alkoxy, and wherein R is alkyl, alkoxy, or

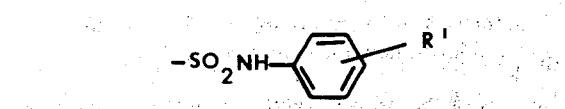

wherein R' is alkyl or alkoxy.

The alkoxy group representing one of the A groups may have from 1–18 carbon atoms, but preferably is a lower alkoxy group. The alkoxy or alkyl group represented by R or R' preferably has at least 5 carbon atoms (so as to provide ballasting characteristics) and may have as many as about 20 carbon atoms.

The present invention also provides silver halide emulsions containing at least one of the above-identified couplers.

The couplers of the present invention and the magenta dyes derived therefrom exhibit improved stability characteristics in comparison to couplers and magenta dyes of the prior art. The magenta dyes prepared by reacting couplers of the invention with any of a number of paraphenylene diamine-type developers exhibit unusually satisfactory light-absorption characteristics. These highly desirable characteristics of the 5-pyrazolone couplers of the present invention are dependent upon the fact that the pyrazolone nucleus bears in the 1-position a 2',6'-dihalo-4'-alkoxyphenyl or a 2',4'-dihalo-6'-alkoxyphenyl substituent, and bears in the 3-position a phenylcarbamylamino substituent.

The particular absorption properties of the magenta dyes prepared from couplers of the invention depend primarily upon the nature of the substituent in the 3-position of the pyrazolone nucleus. If this substituent is a phenylcarbamylamino group having substituted on the phenyl group thereof an alkyl group or an alkoxy group (which groups impart to the molecule non-bleeding characteristics), the resulting dyes have absorption maxima shifted towards lower wavelengths. If this substituent is a phenylcarbamylamino group having substituted on the phenyl group thereof a substituent of the sulfoanilide type substituted with an alkyl or an alkoxy (which groups also impart non-bleeding characteristics to the molecule), the resulting dyes have absorption maxima shifted towards higher wavelengths.

Silver halide photographic emulsions containing couplers of the present invention may readily be prepared by known techniques, such as the solvent dispersion technique described in U.S. Pat. Nos. 2,322,027; 2,801,170; 2,801,171 and others. In addition to hydrophilic colloidal binders such as gelatin, etc., the emulsions may contain such common photographic adjuvants as chemical sensitizers, optical sensitizers, stabilizers, plasticizers, antioxidants, u. v. absorbers, and the like. Silver halide (chloride, bromide, iodide or mixtures thereof) emulsions may have the couplers of the invention added thereto either before or after optical sensitization thereof. The emulsions may be spread on known photographic bases (e.g., polyester film, glass, paper, etc.) to form photographic elements.

The emulsions can be developed with primary aromatic amine developers, e.g., of the paraphenylene diamine type. Developers of this type are exemplified as follows:

Developer 1

| | |
|---|---:|
| Part A | |
| H₂O | 500 ml |
| hydroxylamine hydrochloride | 1 g |
| N,N-diethylparaphenylene diamine sulfate | 2.8 g |
| Part B | |
| H₂O | 500 ml |
| Sodium tripolyphosphate | 2 g |

-continued

Developer 1

| | |
|---|---|
| Anhydrous sodium carbonate | 65 g |
| Anhydrous sodium sulfite | 2.5 g |
| Potassium bromide | 1.2 g |
| Sodium hydroxide | 2 g |

Solution A is poured into solution B to yield the developer bath.

Developer 2

| | | |
|---|---|---|
| Sodium hexametaphosphate | | 2 g |
| Anhydrous sodium sulfite | | 4 g |
| 2-amino-5-diethylaminotoluene hydrochloride | | 3 g |
| Sodium carbonate, monohydrate | | 20 g |
| Potassium bromide | | 2 g |
| Water | to make | 1000 ml. |

Developer 3

| | |
|---|---|
| 2-amino-5-N,N-ethyl,β-methanesulfonamido-ethyl-toluene sulfonate | 4 g |
| Anhydrous sodium sulfite | 2.2 g |
| Sodium hydroxide | 8.5 g |
| Sodium metaborate | 19 g |
| Sodium sulfate | 2 g |

The following examples are illustrative of couplers of the invention:

Coupler 1

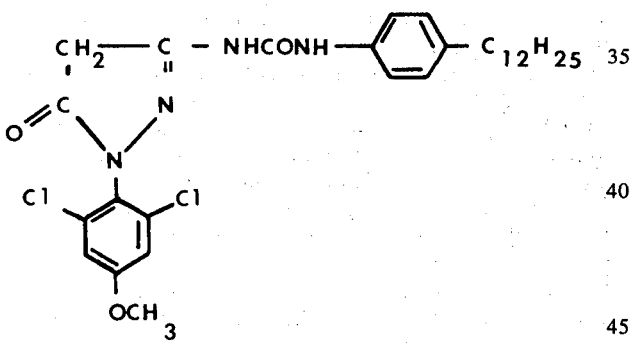

1-(2',6'-dichloro-4'-methoxy)-phenyl-3-p-dodecyl-phenylureido-5-pyrazolone

Coupler 2

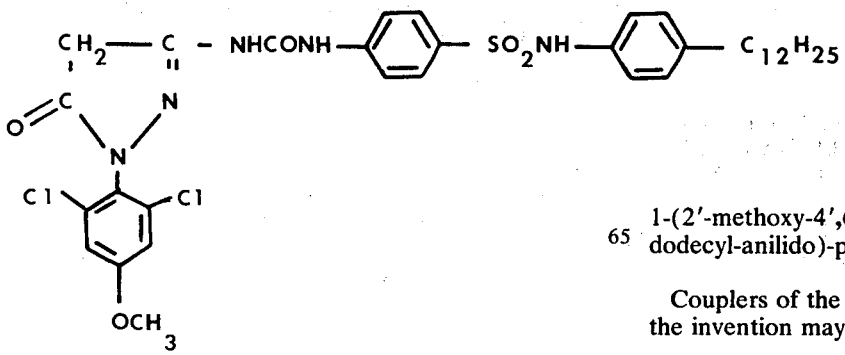

1-(2',6'-dichloro-4'-methoxy)-phenyl-3-[4''-sulfo-p-dodecylanilido]-phenyl-ureido-5-pyrazolone Coupler 3

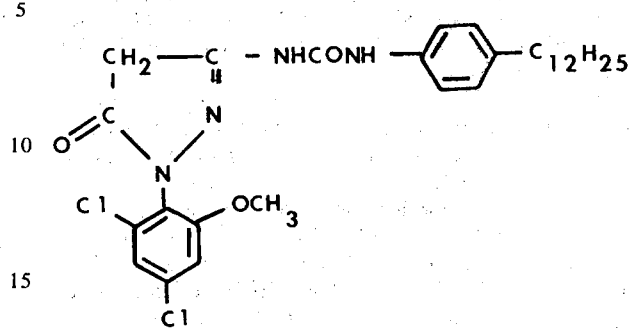

1-(2'-methoxy-4',6'-dichloro)-phenyl-3-p-dodecylphenyl-ureido-5-pyrazolone

Coupler 4

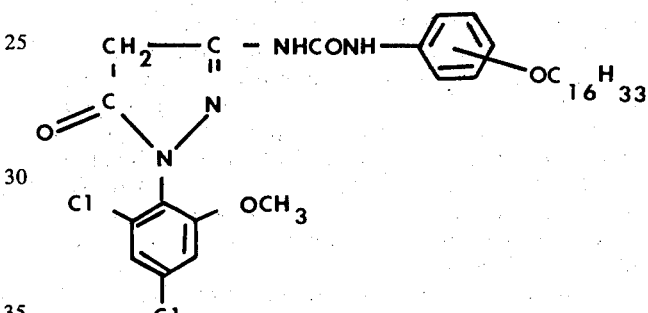

1-(2'-methoxy-4',6'-dichloro)-phenyl-3-m-hexadecyloxyphenylureido-5-pyrazolone

Coupler 5

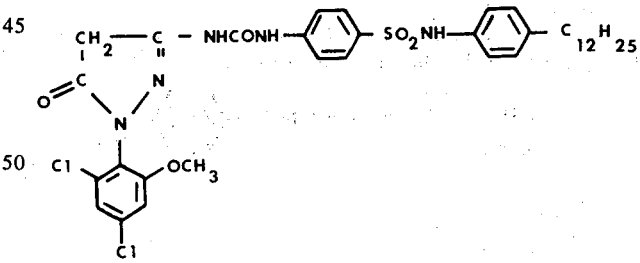

1-(2'-methoxy-4',6'-dichloro)-phenyl-3-(4''-sulfo-p-dodecyl-anilido)-phenyl-ureido-5-pyrazolone Couplers of the prior art with which the couplers of the invention may be compared include:

Coupler 6

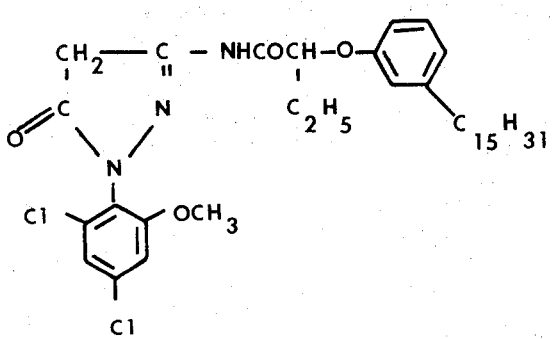

Coupler 7

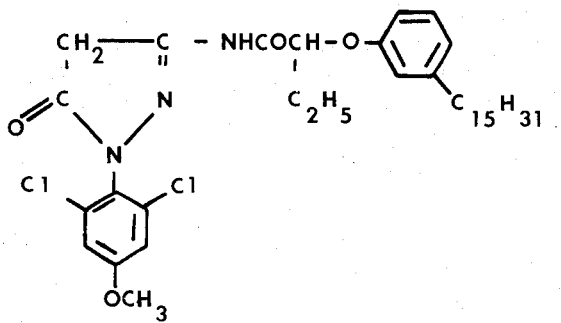

Coupler 8

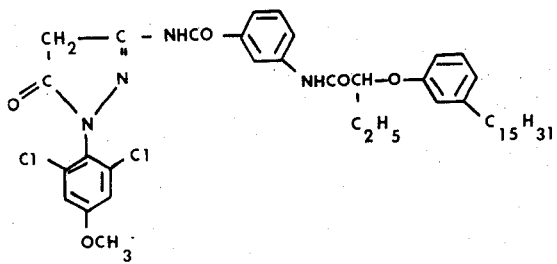

Coupler 9

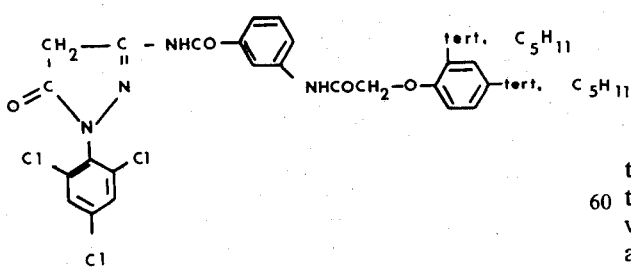

Coupler 10

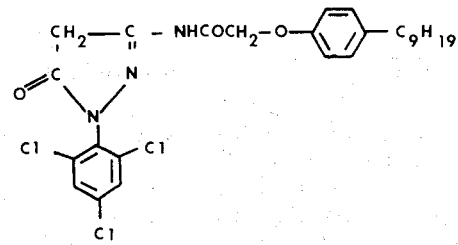

The above couplers 6, 7 and 8 are of the type described in English Patent No. 904,852. Couplers 9 and 10 are of the type described in U.S. Pat. No. 2,600,788.

EXAMPLE I (COUPLER 1)

A. 2,6-dichloro-4-methoxy-aniline

A saturated solution of gaseous HCl in methanol was prepared by bubbling dry gaseous HCl in 2.4 liters of anhydrous methanol with ice-bath cooling. After saturation was complete, 290 g. of p-nitroso phenol (m.p. 133°–136°C, purified by the procedure reported in *Journal of Organic Chemistry*, 32, 1967, p. 156) were added with continuous stirring and bubbling of gaseous HCl through the reaction mass, the temperature of the mass being maintained in the range of 15°–20°C. After stirring for an additional half an hour with bubbling gaseous HCl, the material was filtered, washed with ether and dried. The product was dissolved in 1.5 liters of methanol and 120 ml of water; the solution was refluxed, decolorizing charcoal was added and the filtrate was poured, with stirring, into 10 liters of cold water. The solid was filtered out and the product was crystallized from 800 ml of toluenated methanol to yield 203 g. of 2,6-dichloro-4-methoxy-aniline in the form of fine small white needles melting at 72°–74°C.

B. 2,6-dichloro-4-methoxy-phenyl-hydrazine

A mixture of 140 g. of 2,6-dichloro-4-methomy-aniline, 420 ml of concentrate HCl, and 210 ml of distilled water were vigorously stirred for one hour at room temperature. The mass was then cooled to between +2°C and −2°C, and a solution of 55 g. of sodium nitrite in 160 ml of demineralized water was added dropwise thereto. At the end of the reaction, the mass was stirred for an additional half an hour and the excess of nitrous acid present was destroyed with urea. The resulting solution was rapidly filtered and slowly poured into a solution of 700 g. of $SnCl_2.2H_2O$, 3.5 l. of concentrated HCl and 1.7 l. of demineralized water, maintained at 0°C with stirring. After continued stirring for an additional 4 hours, the mass was permitted to stand undisturbed overnight in a refrigerator. The solid formed was filtered off, washed thoroughly with cold water, and was suspended in 3.0 liters of demineralized water. The mass was cooled to 10°C and made basic under stirring with a 30% NaOH solution, taking care that the temperature did not exceed 12°C. The solid was filtered and extracted with ether, and the extract dried overnight over sodium sulfate. The ether was evaporated to dryness and the residue was crystallized from heptane. 77 g. of the hydrazine having a m.p. of 124°–125°C were obtained. (Analysis: N% Calculated: 13.59; Found 13.53).

C. 1-(2',6'-dichloro-4'-methoxy)-phenyl-3-amino-5-pyrazolone

The so-prepared hydrazine was condensed with β-ethoxy-β-imino-ethyl-propionate to give the 3-aminopyrazolones by the method of U.S. Pat. No. 2,600,788. The product, crystallized by toluenated methanol, melted at 231°–232°C.

Analysis: N% Calculated: 15.32; Found 15.20. Cl% Calculated: 25.54; Found 25.53.

D. Coupler

To 720 ml of pure nitrobenzene were added 232 g. of anhydrous aluminum trichloride in small portions. During this addition the temperature rose to 45°C. Then 240 g. of 1-(2',6'-dichloro-4'-methoxy)-phenyl-3-amino-5-pyrazolone were added in small portions, the temperature rising to 55°C. Thereafter, 252 g. of p-dodecyl-phenyl isocyanate (obtained by phosgenation in toluene of p-dodecyl-aniline) were added dropwise over a one-half hour period. The reaction mixture was maintained at 55°C for 4 hours, and was then poured into 5.0 l. of water and the nitrobenzene was removed by steam distillation, leaving a solid residue. The material was cooled and the solid was recovered by filtration and was dried at 50°C. The dried product melted at 97°–99°C. Crystallization fron anhydrous acetonitrile after treatment with decolorizing charcoal yielded an off-white powder melting at 136°–140°C.

Analysis: C% Calculated: 62.00; Found: 62.2. H% Calculated: 6.89; Found: 6.99. N% Calculated: 9.98; Found: 9.99.

EXAMPLE II (COUPLER 2)

To 112 ml of a 59% by weight solution of 4-sulfo-p-dodecylanilido-phenyl-isocyanate in toluene at 95°C were added 40 g. of the 3-amino pyrazolone of Example I. The resulting solution was refluxed at 110°C for two hours. A 250 ml portion of toluenated methanol was added with great care, when the distillation stabilized an additional 500 ml of methanol were added dropwise and the distillation was continued until 750 ml of distillate had been removed. The material was cooled, poured into a mixture of 3 l. of ice water and 200 ml of concentrated HCl, stirred, filtered, thoroughly washed with water, and dried at 50°C to yield a product melting at 125°–130°C. The product was boiled in petroleum ether, dissolved in benzene and precipitated with ligroin. After filtration the product was triturated in ligroin-petroleum ether (1:1), filtered, and dried at 50°C. A white, fine powder melting at 135°–138°C was obtained.

Analysis: N% Calculated: 9.7; Found: 9.5. S% Calculated: 4.4; Found: 4.2.

EXAMPLE III (COUPLER 3)

The hydrochloride of 4,6-dichloro-2-methomy-aniline was prepared by chlorination in dioxane of orthoanisidine hydrochloride was sulfonyl chloride at a temperature of from room temperature to 40°C for a period of 2–3 hours. The raw product was purified by dissolution in hot methanol, the solution poured in water separated out the 4,6-dichloro-2-methoxy-aniline separating out as a dark oil upon pouring of the solution into water. The oil was extracted with ether and from the extracts (dried on sodium sulfate) the hydrochloride was precipitated out with anhydrous, gaseous hydrochloric acid. The amine which was obtained was diazotized and reduced as described in the preceding preparation to give the corresponding phenylhydrazine which was converted to pyrazolone as described in paragraph C of Example I above. The 1-(2'-methoxy-4',6'-dichloro)-phenyl-3-aminopyrazolone which was obtained melted at 198°–199°C.

Analysis: N% Calculated: 15.32; Found: 15.45. Cl% Calculated: 25.90; Found: 25.90.

The so-prepared product was reacted with p-dodecyl-phenyl-isocyanate using the procedure of Example I to provide a fine white powder melting at 172°–174°C.

Analysis: C% Calculated: 62.00; Found: 61.84. H% Calculated: 6.82; Found: 6,77. N% Calculated: 9.98; Found; 9.96.

EXAMPLE IV (COUPLER 4)

Utilizing the procedure of Example I, 1-(2',4'-dichloro-6'-methoxy)-phenyl-3-amino-pyrazolone was reacted with m-hexadecyl-oxy-phenyl isocyanate (prepared by phosgenation in toluene of the m-hexadecyl-oxy-aniline produced in accordance with French Pat. No. 1,419,647). Crystallization from anhydrous acetonitrile and ethanol yielded the coupler, m.p. 152°–155°C.

Analysis: C% Calculated: 62.50; Found: 62.70. H% Calculated: 7.26; Found: 7.49. N% Calculated: 8.80; Found: 8.70.

EXAMPLE V (COUPLER 5)

Example II was repeated utilizing the 3-amino pyrazolone of Example III. A white powder melting at 128°–132°C was obtained.

EXAMPLE VI

Two grams of each of couplers 1 to 10 were individually dissolved in a solution of 6 ml of butyl phthalate and 12 ml of ethyl acetate, and each solution was then emulsified with 40 ml of a 4% gelatine solution. The resulting emulsions were then diluted with water to 100 ml and a fraction of each emulsion thereof, containing 2 mM of coupler, was mixed with 200 ml of a non-optically sensitized, 7% gelatin-silver bromide-chloride emulsion. The resulting emulsions were each spread on a cellulose acetate base, dried, exposed in a wedge exposimeter, developed with the above-mentioned developers 1 and 2, bleached and fixed.

In Table 1 the absorption maxima of the dyes obtained, expressed in m$\mu$, are shown.

TABLE 1

| Coupler | Developer 1 | Developer 2 |
|---|---|---|
| 1 | 534 | 537 |
| 2 | 540 | 550 |
| 3 | 528 | 534 |
| 4 | 529 | 539 |
| 5 | 536 | 550 |
| 6 | 528 | 536 |
| 7 | 534 | 542 |
| 8 | 536 | 546 |
| 9 | 544 | 550 |
| 10 | 540 | 546 |

FIGS. 1, 2, 3 and 4 are dye absorption curves wherein Log D (Density) is plotted against wavelength.

Figure 2:
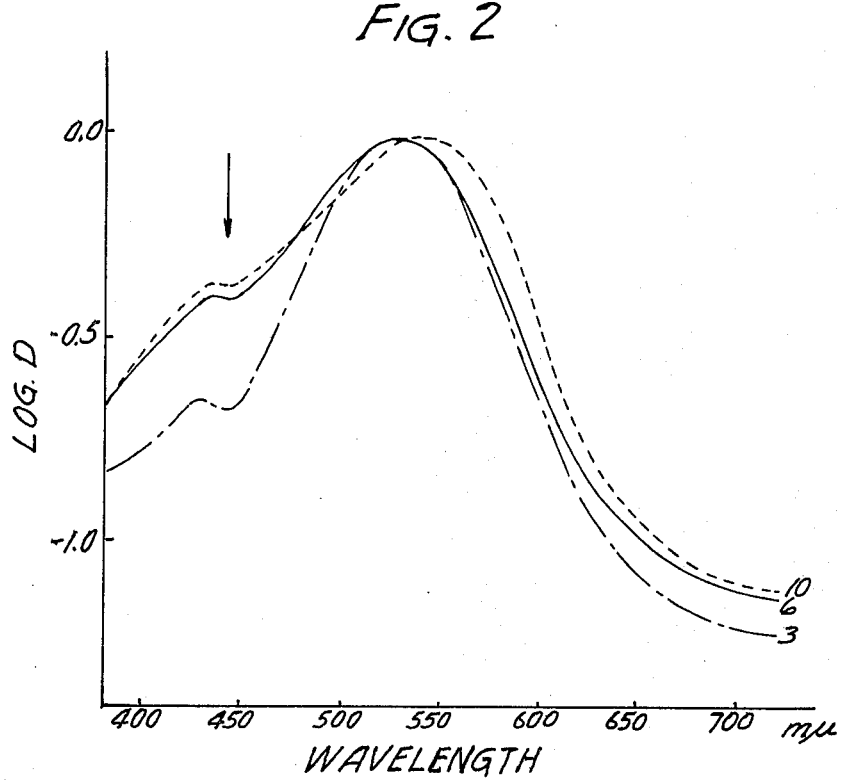

FIGS. 1 and 2 compare the absorption curves of dyes prepared from couplers 5, 6 and 10 and 3, 6 and 10 respectively, each of the dyes being derived from the previously described developer 1. These curves indicate that the dyes resulting from couplers of the invention tend to avoid the unwanted absorption in that area of the spectrum (denoted by the arrows) which is characteristic of the prior art dyes.

Figure 3:
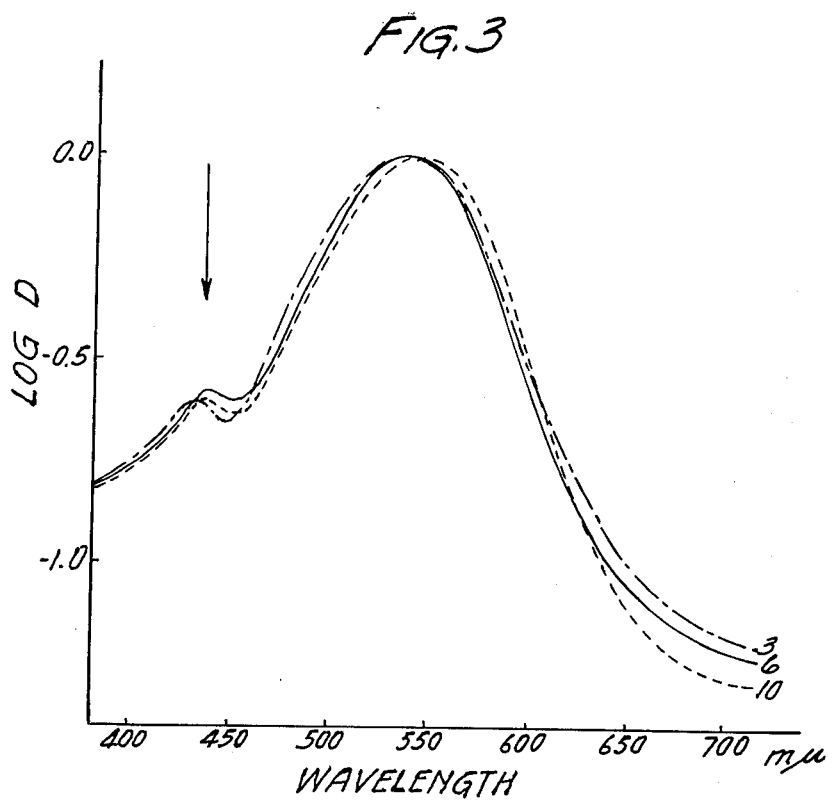
Figure 4:
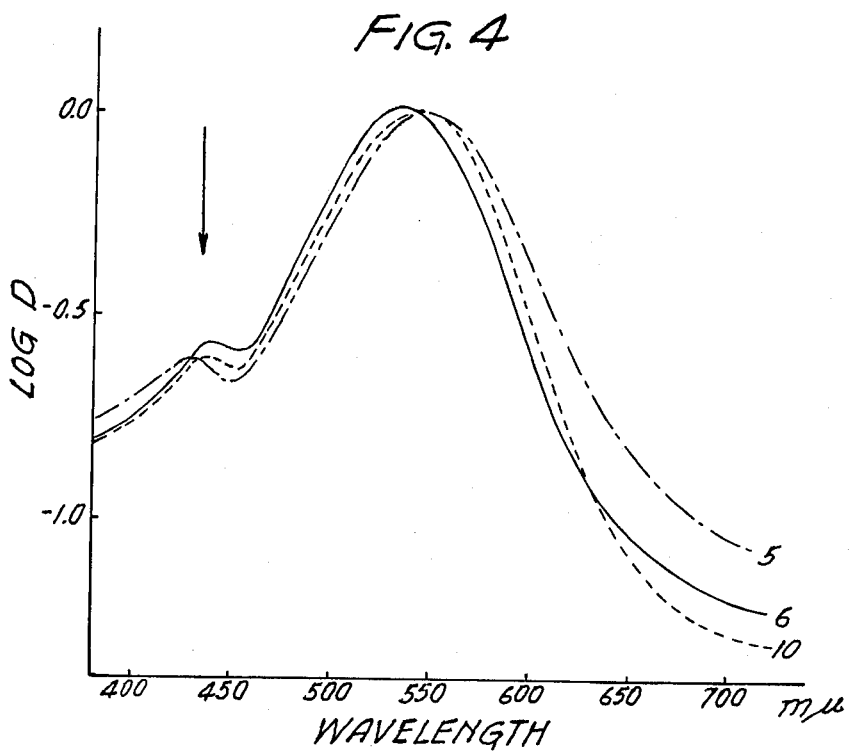

FIGS. 3 and 4 compare the absorption characteristics of dyes prepared from couplers 3, 6 and 10 and 5, 6 and 10 respectively, each dye being derived from the previously described developer 2. These curves indicate that the absorption of the dyes derived from couplers of the invention may conveniently be shifted toward longer or shorter wavelengths to meet the color balance requirements of the materials in which they may be incorporated.

EXAMPLE VII

Six grams of each of couplers 1, 3, 8 and 9 were dissolved in a mixture of 1.8 ml of dibutyl phthalate, 1.8 ml of tricresyl phosphate, and 16 ml of ethyl acetate. Each solution was then emulsified with 60 ml of a 4% gelatin solution and diluted to 100 ml with water. A portion of each dispersion (containing an antioxidizing agent and a U. V. absorber) was added to a non-optically sensitized silver chloride-bromide emulsion to provide a coupler concentration of 35 mM per Kg of emulsion.

Each emulsion was spread on a paper base, dried, exposed in a "shaded wedge" exposimeter, developed with the afore-mentioned developer 3, bleached and fixed. The sensitometric data of Table 2 were derived from fresh images and from images subjected to storage under the indicated conditions.

In comparison to the prior art couplers, the couplers of the invention are thus shown to impart to the emulsion greater sensitivity, contrast and maximum density. Moreover, the couplers of the invention and the dyes prepared therefrom exhibit greater stability than do the compared prior art couplers and dyes.

EXAMPLE VIII

Six grams of each of couplers 1, 8 and 9 were dissolved in a mixture of 3.6 ml of dibutyl phthalate, 3.6 ml of tricresyl phosphate and 16 ml of ethyl acetate. Each solution was emulsified with 60 ml of a 4% gelatin solution and diluted to 100 ml with water, and a portion of each of the resulting dispersions was added to a silver chloride-bromide emulsion (sensitized to green light by addition of an optical sensitizer) to provide a concentration of coupler equal to 35 mM per Kg of emulsion. Each emulsion was spread on a paper base and dried. Some specimens were stored for 7 days at 38°C and 70% R. H. and others were stored for this period at 22°±2°C and 40–45% R. H. Each specimen was then developed with the above-described developer 3, bleached and fixed, and the differences between the two sets of specimens were evaluated. The pertinent data are set out in Table 3.

What we claim is:

1. A color coupler of the formula:

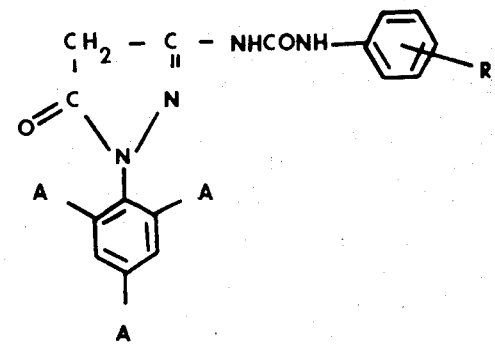

wherein two of the A groups are halogen, the remaining A group is alkoxy of 1-18 carbon atoms, and R and $R^1$ are alkoxy or alkyl groups of 5-20 carbon atoms.

2. A coupler according to claim 1 of the formula

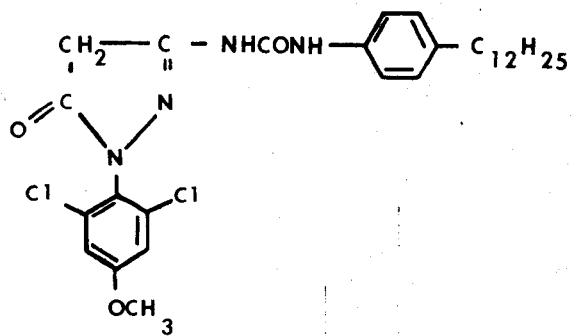

TABLE 2

| Coupler | Non-stored image | | | | | Stored image | | | | Stored 24 hours at 90°C and 70% R. H. |
| | | | | | | Exposure in fadometer (xenon lamp) | | | | |
| | Sr | γ | Do B | Do G | D max | D 20 h | D 40 h | ΔDoB 20 h | ΔDoB 40 h | ΔD |
|---|---|---|---|---|---|---|---|---|---|---|
| 1 | 1.13 | 2.70 | 0.10 | 0.06 | 2.70 | −0.06 | −0.41 | +0.03 | +0.07 | −0.03 |
| 3 | 1.08 | 2.60 | 0.10 | 0.07 | 2.60 | −0.05 | −0.38 | +0.03 | +0.10 | −0.08 |
| 8 | 1.34 | 2.40 | 0.07 | 0.04 | 2.40 | −0.04 | −0.45 | +0.05 | +0.11 | −0.14 |
| 9 | 1.37 | 2.45 | 0.10 | 0.05 | 2.50 | −0.09 | −0.59 | +0.08 | +0.20 | −0.14 |

Sr = relative sensitivity expressed in log It required to provide a density of 1.0;
γ = contrast;
Do = minimum density (fog) measured under blue light (B) and green light (G)
Dmax = maximum density
ΔD = maximum density differential
ΔDoB = fog differential measured under blue light (indicating stability of residual coupler)

3. A coupler according to claim 1 of the formula
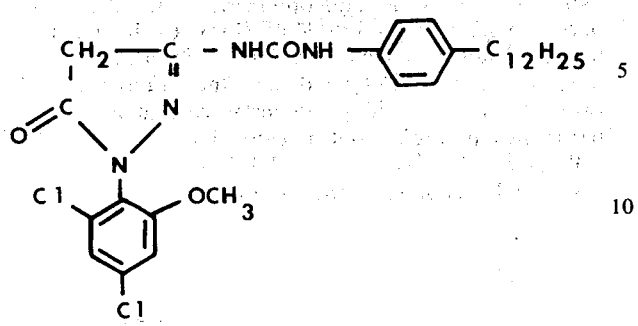
4. A coupler according to claim 1 of the formula
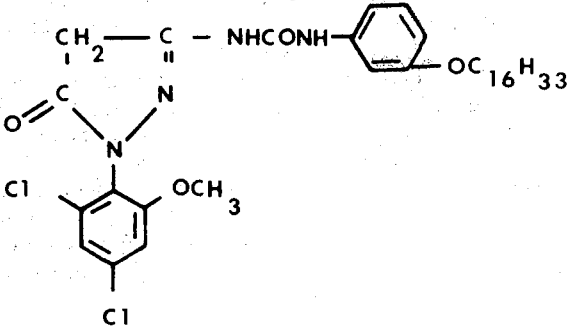
* * * * *